United States Patent [19] [11] 4,404,020
Schurter et al. [45] Sep. 13, 1983

[54] CERTAIN ESTERS OF 2-[(2,6-DICHLORO-3-PYRIDYL)OXY]PROPIONIC ACID, COMPOSITIONS CONTAINING SAME AND THEIR HERBICIDAL PROPERTIES

[75] Inventors: Rolf Schurter, Binningen, Switzerland; Niels Clauson-Kaas, Farum, Denmark; Hermann Rempfler, Binningen, Switzerland

[73] Assignee: Ciba-Geigy Corporation, Ardsley, N.Y.

[21] Appl. No.: 323,604

[22] Filed: Nov. 20, 1981

Related U.S. Application Data

[63] Continuation of Ser. No. 36,265, May 4, 1979, abandoned, which is a continuation of Ser. No. 862,697, Dec. 21, 1977, abandoned, which is a continuation-in-part of Ser. No. 715,352, Aug. 18, 1976, abandoned.

[30] Foreign Application Priority Data

Aug. 25, 1975 [CH] Switzerland .................. 10964/75

[51] Int. Cl.³ .................. C07D 213/65; A01N 43/40
[52] U.S. Cl. .................. 71/94; 546/302; 542/438
[58] Field of Search .................. 546/302; 542/438; 71/94

[56] References Cited
FOREIGN PATENT DOCUMENTS
452528 5/1968 Switzerland .................. 544/105

OTHER PUBLICATIONS

Cava et al., Chem. Abstracts, vol. 53, (18), 18026f to 18,027e Sep. 25, 1959.
Cave et al., Journal of Organic Chemistry, vol. 23, pp. 1614-1616, (1958).
Borje, Chem. Abstracts, vol. 74, (25) Jun. 21, 1971.
Mertes et al., Chem. Abstracts, vol. 68, (25), 114,371f Jun. 17, 1968.

Primary Examiner—Alan L. Rotman
Attorney, Agent, or Firm—Frederick H. Rabin; Harry Falber

[57] ABSTRACT

This invention relates to 3-pyridinol compounds corresponding to formula I

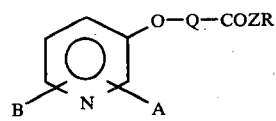

wherein
A is halogen, alkyl or cyano
B is halogen
Q is an aliphatic bridge that can also be unsaturated, branched or substituted
R is hydrogen, an aliphatic, cycloaliphatic, aromatic or heterocyclic radical, a metal ion or a quaternary ammonium group,
Z is oxygen or sulfur, processes for producing them, their use for regulating plant growth, and to compositions containing these compounds.

12 Claims, No Drawings

CERTAIN ESTERS OF 2-[(2,6-DICHLORO-3-PYRIDYL)OXY]PROPIONIC ACID, COMPOSITIONS CONTAINING SAME AND THEIR HERBICIDAL PROPERTIES

This is a continuation of application Ser. No. 036,265 filed on May 4, 1979 now abandoned, which is a continuation of application Ser. No. 862,697 filed on Dec. 21, 1977, now abandoned, which in turn was a continuation-in-part of application Ser. No. 715,352 filed on Aug. 18, 1976, now abandoned.

BACKGROUND OF THE INVENTION, DESCRIPTION OF THE PRIOR ART

This invention discloses acid derivatives of ring substituted 3-hydroxy-pyridines.

These compounds are new and show a plant growth regulatory activity, which can be usefully exploited in the agricultural field. The art discloses compounds with similar chemical structure, but which to our knowledge have not been tested or commercially exploited for plant growth regulation.

In Acta Chem. Scand. 23 (1969) p 1791–1796, there is disclosed a way to synthetise such 3-alkoxypyridines by way of alkylation of 3-pyridinols in dimethyl sulfoxide. In the J. Heterocyclic Chem. 5 (1968) p 281–283, we find the ethyl ester of α-(3-pyridyloxy)-propionic acid and of 3-pyridyloxy acetic acid disclosed as novel intermediate products in the synthesis of furo-[2,3-c]pyrimidine. In these articles there is given no indication about a possible use for these compounds, which are structurally closest to the ones disclosed in this invention.

These ist an article in the J. Org. Chem. 23 (1958) p 1614–1616, wherein the acid and ethyl esters of some 2-pyridyloxy acetic acids substituted by chlorine and bromine in the pyridyl ring were synthetised in order to be compared for their herbicidal activity with herbicides, such as 2,4-dichlorophenoxy acetic acid and 2,4,5-trichlorphenoxy acetic acid.

Further compounds with vaguely similar chemical structure have also become known as biocidal, microbiocidal and fungicidal agents or as agents for combatting animal pests or enteroparasites, see the U.S. Pat. No. 3,249,619 or the German Offenlegungsschrift No. 2 103 728. Similar 2-pyridinol compounds are described as herbicides in the U.S. Pat. Nos. 3,671,486 and 3,755,339.

SUMMARY OF THE INVENTION

A group of novel compounds, halogen substituted 3-pyridyloxyalkane carboxylic acid aid esters are disclosed, which are structurally different from the ones disclosed in the prior art. They proved to have a plant regulating activity. They inhibit or slow down the growth of plants, which can be usefully exploited in the agriculture for example for the reduction of the vegetative growth of soya-bean plants and of similar leguminosae, which results in an increase in the yield of these crops; the inhibition of the undesirable growth of side shoots in the case of tobacco plants, the leading shoots of which have been cut, which inhibition promotes the formation of larger and better leaves or the inhibition of the growth of large dicotyledonous plants, such as fruit trees, ornamental trees, bushes and hedges, with the object of reducing the extent of cutting operations.

DETAILED DISCLOSURE

The present invention relates to new 3-pyridinol compounds, a process for producing them, to the use of these 3-pyridinol compounds for regulating plant growth, and to plant-regulating compositions containing such compounds as active substance.

The pyridinol compounds correspond to formula I,

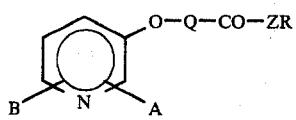

(I)

wherein
A is a halogen atom, the methyl or cyano group
B is a halogen atom
Q is a branched- chain or straight chain alkylene or alkylene or alkenylene bridge, having up to 12 carbon atoms, which can be substituted by halogen, phenyl, the carboxyl or a $C_1$-$C_4$ alkoxycarbonyl radical;
Z is oxygen or sulphur
R is hydrogen, an alkali metal cation, a quaternary $C_1$-$C_4$ alkyl or hydroalkyl ammonium group; a $C_1$-$C_{18}$ alkyl group, that is unsubstituted or substituted by halogen, $C_1$-$C_4$ alkoxy, phenyl, unsubstituted or mono- or polysubstituted by halogen $C_1$-$C_4$ alkyl, $C_1$-$C_4$ alkoxy or alkylthio, or by furan or tetrahydrofuran; $C_5$-$C_7$ cyclohexyl; $C_3$-$C_8$ alkenyl, unsubstituted or substituted by halogen; $C_3$-$C_8$ alkynyl; phenyl unsubstituted or mono- or polysubstituted by halogen, $C_1$-$C_4$ alkyl, $C_1$-$C_4$ alkoxy or alkylthio, cyano or nitro; pyridine or dihydro thiazole.

Alkyl radicals in this formula, also as moiety of alkoxy or alkylthio groups, are both branched-chain and straight-chain alkyl radicals having the given number of carbon atoms. The alkenyl and alkynyl radicals can contain 3 to 12 carbon atoms; they are however preferably allyl, methallyl and propargyl radicals.

The alkylene bridge member Q can contain up to 12 C atoms; it is preferably methylene, 1- or 2-alkylene or the 2-propylene bridge. The alkenylene bridge member is preferably a vinylene, alkylene or methallylene group. These groups can be substituted by halogen atoms, a phenyl group or a —COOR group.

The 3-pyridinol compounds of formula I are produced by reaction of a 3-pyridinol of formula II

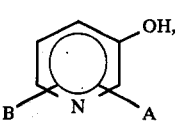

(II)

wherein A and B have the given meanings, with a halogen derivative of formula III Hal—Q—CO—ZR         (III)

wherein Hal is a halogen atom, preferably chlorine or bromine, Q, Z and R have the given meanings, in the presence of a basic condensation agent and optionally in a polar solvent.

The said compounds can be produced also by addition of a 3-pyridinol of formula II with a compound of formula IV $$Q'—CO—ZR \quad (IV)$$

wherein —ZR has the given meaning and Q' is a twofold or threefold unsaturated bridge member having up to 12 carbon atoms. Q' can be an alkylene bridge member or an alkynylene group, for example ethynyl, propargyl, methylpropargyl, butynyl, etc.

This condensation is preferably performed in an anhydrous inert solvent.

Compounds of formula I in which —ZR is the hydroxyl group can be converted by known methods to esters or thioesters either directly or by way of the corresponding acid halide. They can likewise be readily converted into metal salts or quaternary ammonium salts. Such conversions of the function Z are well known and need no further explanation.

Where they are not known, starting materials of formula II can be produced by the following methods and according to the given references.

3-Hydroxy-6-methylpyridine is produced from furfurylamine and formaldehyde by reaction with $HCl/H_2O$: see in this respect N. Clauson-Kaas et al., Acta. Chem. Scand. 21 (1967) 1104, as well as the British Patent Specification No. 862,581 or the German Patent Specification available for inspection No. 1,134,376. It can be subsequently converted by nitration and/or halogenation into other starting materials.

5-Chloro-3-hydroxypyridine can be produced from furfurylamine by reaction with chlorine/water. Another method is described in Czuba, Rocz. Chem. 34 (1960) 905-15.

3-Hydroxypyridine derivatives containing in the 2-position a cyano or amide function can be obtained according to the British patent specification No. 1,038,342 or according to N. Clauson-Kaas et al., Acta. Chem. Scand. 23 (1969), 1785.

2,6-Dichloro-3-hydroxypyridine can be produced from 3-hydroxypyridine by nitration in the 2-position, subsequent reaction with hydrochloric acid and chlorination in the 6-position.

Suitable starting materials of Formula III are acids, esters and thiol esters of halogenated lower fatty acids having up to 12 carbon atoms; thus, e.g., chloro- and bromoacetic acid esters, esters of 2- and 3-chloro- and bromopropionic acid and of correspondingly halogenated further saturated and unsaturated fatty acids, and esters and thiol esters thereof. The corresponding fluoro- or iodocarboxylic acids and esters were naturally also suitable for this reaction, but they are less easily available than chloro or bromic acids.

The 3-pyridinol compounds of the present invention have a regulating action on plant growth; in particular they inhibit the growth of dicotyledonous plants. Examples of the profitable application of the 3-pyridinol compounds according to the invention are, for example, the reduction of the vegetative growth of soya-bean plants and of similar leguminosae, which results in an increase in the yield of these crops; the inhibition of the undesirable growth of side shoots in the case of tobacco plants, the leading shoots of which have been cut, which inhibition promotes the formation of larger and better leaves; and the inhibition of the growth of large dicotyledonous plants, such as fruit trees, ornamental trees, bushes and hedges, with the object of reducing the extent of cutting operations.

The compounds of the present invention are negligibly toxic for warm-blooded animals, and the application of these compounds presents no problems. The amount to be applied is between 0.1 and 5 kg per hectare.

The compounds of the present invention are novel compounds. To our knowledge they have not been used in the field of agricultural chemistry. The production of some quite similar 3-pyridinol compounds is described in Acta. Chem. Scand. 23 (1969) pp. 1791-1796 and in J. Hterocycl. Chem. 5 (1968) p. 281-283. Further such compounds have become known also as biocidal, microbiocidal and fungicidal agents, or as agents for combatting animal pests or enteroparasites, see the U.S. Pat. No. 3,249,619 or the German Offenlegungsschrift No. 2 103 728. Similar 2-pyridinol compounds are also described as herbicidal in the U.S. Pat. Nos. 3,761,486 and 3,755,339.

Compounds which have proved particularly effective in inhibiting the growth of dicotyledonous plants are the compounds the formula V

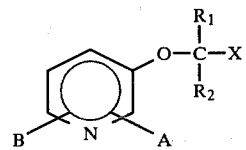

wherein

A, B, have the meaning given above under formula I $R_1$ is hydrogen or $C_1$-$C_3$ alkyl $R_2$ is hydrogen, the carboxyl or an $C_1$-$C_4$ alkoxycarbonyl x is group $OR_3$ or $SR_4$ $R_3$ is hydrogen an alkalimetal cation or a quaternary $C_1$-$C_4$ alkyl or hydroxyalkyl ammonium group; $C_1$-$C_{12}$ alkyl unsubst. or substituted by halogen, $C_1$-$C_4$ alkoxy, phenyl unsubstituted or mon or polysubstituted by halogen, $C_1$-$C_4$ alkyl, $C_1$-$C_4$ alkoxy or alkylthio; $C_5$-$C_7$ cycloalkyl; $C_3$-$C_8$ alkenyl unsubstituted or substituted by halogen; $C_3$-$C_8$ alkenyl; phenyl, unsubstituted, mono or polysubstituted by halogen, $C_1$-$C_4$ alkyl, $C_1$-$C_4$ alkoxy or alkylthio, cyano or nitro;

$R_4$ is hydrogen, $C_1$-$C_{12}$ alkyl unsubstituted or substituted by halogen, $C_1$-$C_4$ alkoxy, phenyl, mono or polysubstituted by halogen $C_1$-$C_4$ alkyl, $C_1$-$C_4$ alkoxy or alkylthio; $C_5$-$C_7$ cycloalkyl; $C_3$-$C_8$ alkenyl, unsubstituted or substituted by halogen; $C_3$-$C_8$ alkynyl; phenyl, unsubstituted, mono- or polysubstituted by halogen, $C_1$-$C_4$ alkyl, $C_1$-$C_4$ alkoxy or alkylthio, cyano or nitro.

Of those the most effective compounds where those, wherein A and B each represent a halogen atom and/or those, wherein Q is the methylene or α-ethylene bridge

and Z is oxygen in formula I.

EXAMPLE 1

2-[(2,6-dichloro-3-pyridyl)oxy]propionic acid ethyl ester 164 g (1 mole) of 2,6-dichloro-3-pyridinol, 1500 ml of acetonitrile, 253.4 g (1.4 moles) of 2-bromopropionic acid ethyl ester and 127.2 (1.2 moles) of sodium carbonate were refluxed for 3 hours. The reaction mixture was then cooled, filtered and concentrated in a rotary evaporator. The residue was taken up in ether and washed with 2 N sodium hydroxide solution. After drying with magnesium sulphate and concentration of the solution by evaporation, distillation was performed, with a clear oil distilling at 110°–140°/0.1 torr; yield: 200 g; $n_D^{25}$:1.5200. Crystallisation from benzene/petroleum ether yielded a product having the melting point 41°–46°.

The 2,6-dichloro-3-pyridinol required as starting material was produced as follows:

(a) 2,6-dichloro-3-pyridinol 100 g (0.77 mole) of 2-chloro-3-pyridinol (I) was dissolved in 350 ml of dimethylformamide. 70 ml of chlorine (measured at −80°; 0.93 mole) was introduced in the course of 1.5 hours into the stirred solution at 0°. The reaction mixture was then stirred for 1.5 hours at 20° C. and subsequently concentrated in a rotary evaporator (bath: 50°; 10 torr). 400 ml of water and 100 ml of ether were added to the residue; the two phases were separated and the aqueous phase was extracted 5 times with 100 ml of ether each time. The combined ether phases were washed with water and dried. The solvent was removed in vacuo; the semisolid residue was stirred with 1.6 liters of water, and the resulting suspension was adjusted to pH 3. The suspension was heated to boiling, and after a few minutes the solution was decanted from an oily residue. The solution was purified with active charcoal, and the yellow product obtained on cooling was recrystallised from water; m.p. 136°–138° C.; yield 42 g.

EXAMPLE 2

2-[(2,6-dichloro-3-pyridyl)oxy]propionic acid 105 g of 2-[(2,6-dichloro-3-pyridyl)oxy]propionic acid ethyl ester was refluxed with 550 ml of 1 N sodium hydroxide solution for 1 hour. The pH value of the solution was brought to 1.5 with concentrated hydrochloric acid and then filtered. Recrystallisation from ethanol/water yielded 58 g of the above acid, m.p. 128°–131°.

EXAMPLE 3

2-[(2,6-dichloro-3-pyridyl)oxy]propionic acid methyl ester 12.75 g (0.05 mole) of 2-[(2,6-dichloro-3-pyridyl)oxy]propionic acid chloride in 75 ml of ether was slowly added dropwise at room temperature to a stirred solution, cooled with ice to 0°, of 1.6 g (0.05 mole) of methanol, 50 ml of ether and 4.0 g (0.05 mole) of pyridine. After completion of the addition, the reaction solution was stirred for one hour at room temperature and subsequently filtered through silica gel. The ethereal solution was then washed with 1 N sodium hydroxide solution, dried with magnesium sulphate and concentrated in a rotary evaporator. The residue was recrystallised from diisopropyl ether to obtain a product having a melting point of 65°.

The acid chloride used as starting material was obtained as follows:

(a) 2-[(2,6-dichloro-3-pyridyl)oxy]propionic acid chloride 23.6 g (0.1 mole) of 2-[(2,6-dichloro-3-pyridyl)oxy]propionic acid, 150 ml of chloroform and 1.5 ml of dimethylformamide were heated with stirring at 55°, and an addition was then made dropwise in the course of 1 hour of a solution of 18 g (0.15 mole) of thionyl chloride in 40 ml of chloroform. The reaction mixture was subsequently refluxed for 16 hours and afterwards concentrated in vacuo. The resulting product was used directly for further reactions.

TABLE I

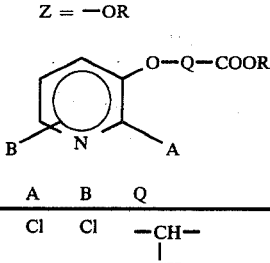

Z = —OR

Except where otherwise indicated, A is in the 2-position and B in the 6-position of the pyridine ring.

| No. | A | B | Q | R | Physical constants |
|---|---|---|---|---|---|
| 1 | Cl | Cl | —CH—<br>│<br>CH$_3$ | —CH$_3$ | m.p. 65° Example 3 |
| 2 | Cl | Cl | —CH—<br>│<br>CH$_3$ | iso C$_3$H$_7$ | m.p. 58° |
| 3 | Cl | Cl | —CH—<br>│<br>CH$_3$ | —CH(C$_2$H$_5$)$_2$ | m.p. 50–51° |
| 4 | Cl | Cl | —CH—<br>│<br>CH$_3$ | —C$_8$H$_{17}$ | $n_D^{25}$ 1.4980 |
| 5 | Cl | Cl | —CH—<br>│<br>CH$_3$ | —C$_2$H$_4$Br | $n_D^{25}$ 1.5468 |
| 6 | Cl | Cl | —CH—<br>│<br>CH$_3$ | —C$_6$H$_{12}$Cl | $n_D^{25}$ 1.5200 |

TABLE I-continued

Z = —OR

Except where otherwise indicated, A is in the 2-position and B in the 6-position of the pyridine ring.

| No. | A | B | Q | R | Physical constants |
|---|---|---|---|---|---|
| 7 | Cl | Cl | —CH(CH₃)— | —CH₂CCl₃ | $n_D^{25}$ 1.5388 |
| 8 | Cl | Cl | —CH(CH₃)— | —C₂H₄OCH₃ | $n_D^{25}$ 1.5186 |
| 9 | Cl | Cl | —CH(CH₃)— | —C₂H₄OC₄H₉ | $n_D^{25}$ 1.5043 |
| 10 | Cl | Cl | —CH(CH₃)— | —C₃H₆—C₆H₅ | $n_D^{25}$ 1.5557 |
| 11 | Cl | Cl | —CH(CH₃)— | —CH₂-(tetrahydrofuryl) | $n_D^{25}$ 1.5260 |
| 12 | Cl | Cl | —CH(CH₃)— | —CH—CH=CH₂ | m.p. 33° |
| 13 | Cl | Cl | —CH(CH₃)— | C₂H₄C≡CC₂H₅ | $n_D^{25}$ 1.5245 |
| 14 | Cl | Cl | —CH(CH₃)— | —CH₂—C₆H₅ | m.p. 81° |
| 15 | Cl | Cl | —CH(CH₃)— | —CH₂—C₆H₄—OCH₃ | m.p. 67° |
| 16 | Cl | Cl | —CH(CH₃)— | —CH₂—C₆H₄—CH₃ | m.p. 72° |
| 17 | Cl | Cl | —CH(CH₃)— | —CH₂—C₆H₄—Cl | m.p. 79° |
| 18 | Cl | Cl | —CH(CH₃)— | cyclohexyl | m.p. 49–51° |
| 19 | Cl | Cl | —CH(CH₃)— | —C₆H₅ | m.p. 62° |
| 20 | Cl | Cl | —CH(CH₃)— | —C₆H₄—Br | m.p. 85° |
| 21 | Cl | Cl | —CH(CH₃)— | —C₆H₄—C(CH₃)₃ | $n_D^{30}$ 1.5475 |
| 22 | Cl | Cl | —CH(CH₃)— | —C₆H₄—NO₂ | m.p. 121–122° |

TABLE I-continued

Z = —OR

Structure: pyridine ring with B at 6-position, A at 2-position, and O—Q—COOR at 3-position.

Except where otherwise indicated, A is in the 2-position and B in the 6-position of the pyridine ring.

| No. | A | B | Q | R | Physical constants |
|---|---|---|---|---|---|
| 23 | Cl | Cl | —CH(CH$_3$)— | 2-CH$_3$-phenyl | m.p. 122° |
| 24 | Cl | Cl | —CH(CH$_3$)— | 4-SCH$_3$-phenyl | |
| 25 | Cl | Cl | —CH(CH$_3$)— | H | m.p. 128–131° (Example 2) |
| 26 | Cl | Cl | —CH(CH$_3$)— | —C$_2$H$_5$ | m.p. 45–46° (Example 1) |
| 27 | Cl | Cl | —CH(C$_2$H$_5$)— | H | m.p. 143° |
| 28 | Cl | Cl | —CH(C$_2$H$_5$)— | —C$_2$H$_5$ | n$_D^{20}$ 1.5180 |
| 29 | Cl | Cl | —C$_3$H$_6$— | H | m.p. 115° |
| 30 | Cl | Cl | —C(CH$_3$)=CH— | H | m.p. 175–179° |
| 31 | Cl | Cl | —C(CH$_3$)=CH— | —C$_2$H$_5$ | m.p. 91–92° |
| 32 | Br | Br | —CH(CH$_3$)— | —C$_2$H$_5$ | m.p. 57–59° |
| 33 | Br | Br | —CH(CH$_3$)— | H | m.p. 122–124° |
| 34 | Cl | Br | —CH(CH$_3$)— | —C$_2$H$_5$ | m.p. 48° |
| 35 | Cl | Br | —CH(CH$_3$)— | H | m.p. 123–124° |
| 36 | Cl | CH$_3$ | —CH$_2$— | H | m.p. 179–180° |
| 37 | Cl | CH$_3$ | —CH(CH$_3$)— | —C$_2$H$_5$ | b.p. 97°/0.07 torr |
| 38 | Cl | CH$_3$ | —CH(CH$_3$)— | H | m.p. 160–162° |
| 39 | Cl | CH$_3$ | —CH$_2$— | —C$_2$H$_5$ | m.p. 40–42° |
| 40 | Cl | Cl | —CH(phenyl)— | —C$_2$H$_5$ | n$_D^{25}$ 1.5655 |

TABLE I-continued

Z = —OR

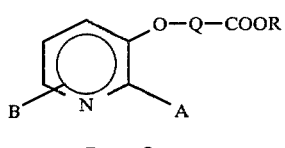

Except where otherwise indicated, A is in the 2-position and B in the 6-position of the pyridine ring.

| No. | A | B | Q | R | Physical constants |
|---|---|---|---|---|---|
| 41 | Cl | Cl | —CCl—CH$_2$—<br>$\quad\ \ $\|<br>$\quad\ \ $CH$_3$ | —C$_2$H$_5$ | |
| 42 | Cl | Cl | —CH$_2$— | —C$_8$H$_{17}$ | |
| 43 | Cl | Cl | —CH—<br>$\ \ $\|<br>$\ \ $CH$_3$ | —C$_{12}$H$_{23}$ | n$_D^{20}$ 1.4955 |
| 44 | Cl | Cl | —CH—<br>$\ \ $\|<br>$\ \ $CH$_3$ | —C$_{18}$H$_{37}$ | m.p. 43–44° |
| 45 | Cl(4) | Cl | —CH—<br>$\ \ $\|<br>$\ \ $CH$_3$ | —C$_2$H$_5$ | |
| 46 | Cl(4) | Cl | —CH—<br>$\ \ $\|<br>$\ \ $CH$_3$ | H | |
| 47 | Cl | Cl | —CH—<br>$\ \ $\|<br>$\ \ $C$_8$H$_{17}$ | —C$_2$H$_5$ | n$_D^{25}$ 1.4990 |
| 48 | Cl | Cl | —CH—<br>$\ \ $\|<br>$\ \ $C$_8$H$_{17}$ | H | m.p. 69° |
| 49 | Cl | Cl | —(CH$_2$)$_{10}$— | —C$_2$H$_5$ | n$_D^{27}$ 1.5020 |
| 50 | Cl | Cl | —(CH$_2$)$_{10}$— | H | m.p. 87° |
| 51 | Cl | Cl | —C—<br>$\ \ $‖<br>$\ \ $C(CH$_3$)$_2$ | —C$_2$H$_5$ | b.p. 105°/0.01 |
| 52 | Cl | Cl | —CH—<br>$\quad\ \ $\|<br>$\quad\ \ $C$_6$H$_5$ | H | m.p. 153–156° |
| 53 | Cl | Cl | —C$_3$H$_6$— | —C$_2$H$_5$ | m.p. 33–34° |
| 54 | Cl | Cl | —CH$_2$— | H | m.p. 147–149° |
| 55 | Cl | Cl | —CH$_2$— | CH$_3$ | m.p. 80–82° |
| 56 | Cl | Br | —CH—<br>$\ \ $\|<br>$\ \ $CH$_3$ | CH$_3$ | m.p. 66° |
| 57 | Cl | Br | —C$_3$H$_6$— | —C$_2$H$_5$ | m.p. 51° |
| 58 | Cl | Br | —CH—<br>$\ \ $\|<br>$\ \ $C$_2$H$_5$ | —C$_2$H$_5$ | m.p. 33° |
| 59 | Cl | Br | —CH—<br>$\ \ $\|<br>$\ \ $C$_8$H$_{17}$ | —C$_2$H$_5$ | m.p. 39° |
| 60 | Cl | Br | —C$_3$H$_6$— | H | m.p. 121° |
| 61 | Cl | Br | —CH—<br>$\ \ $\|<br>$\ \ $C$_2$H$_5$ | H | m.p. 133° |
| 62 | Cl | Br | —CH—<br>$\ \ $\|<br>$\ \ $C$_8$H$_{17}$ | H | m.p. 75° |

TABLE I-continued

Z = —OR

Except where otherwise indicated, A is in the 2-position and B in the 6-position of the pyridine ring.

| No. | A | B | Q | R | Physical constants |
|---|---|---|---|---|---|
| 63 | Cl | Cl | —C(CH₃)(COOH)— | H | m.p. 149° |
| 64 | Cl | Br | —C(CH₃)(COOC₂H₅)— | —C₂H₅ | $n_D^{25}$ 1.5105 |
| 65 | Cl | Br | —C(CH₃)(COOH)— | H | m.p. 145° |
| 66 | Cl | Cl | —C(CH₃)(COOC₂H₅)— | —C₂H₅ | $n_D^{20}$ 1.5065 |
| 67 | CN | Cl | —CH(CH₃)— | —C₂H₅ | |
| 68 | Cl | Cl | —CH(CH₃)— | Na⊕ | |
| 69 | Cl | Cl | —CH(CH₃)— | H₂N⊕(C₂H₄OH)₂ | m.p. 65–70° |
| 70 | Cl | Cl | —CH(CH₃)— | HN⊕(nC₄H₉)₃ | $n_D^{30}$ 1.5050 |

TABLE 2

Z = SR

Except where otherwise indicated, A is in the 2-position and B in the 6-position of the pyridine ring.

| No. | A | B | Q | R | Physical constants |
|---|---|---|---|---|---|
| 1 | Cl | Cl | —CH(CH₃)— | sec.C₄H₉ | $n_D^{20}$ 1.5456 |
| 2 | Cl | Cl | —CH(CH₃)— | —C₆H₅ | |
| 3 | Cl | Cl | —CH(CH₃)— | cyclohexyl | $n_D^{30}$ 1.5588 |
| 4 | Cl | Cl | —CH(CH₃)— | —CH₂C₆H₅ | |
| 5 | Cl | Cl | —CH(CH₃)— | H | |
| 6 | Cl | Cl | —CH(CH₃)— | —C₂H₅ | $n_D^{20}$ 1.5592 |
| 7 | Cl | Cl | —CH(CH₃)— | n-C₃H₇ | |
| 8 | Cl | Cl | —CH(CH₃)— | isoC₃H₇ | $n_D^{20}$ 1.5512 |

TABLE 2-continued

Z = SR

Except where otherwise indicated, A is in the 2-position and B in the 6-position of the pyridine ring.

| No. | A | B | Q | R | Physical constants |
|---|---|---|---|---|---|
| 9 | Cl | Cl | —CH(CH₃)— | —C₅H₁₁ | $N_D^{20}$ 1.5422 |
| 10 | Cl | Cl | —CH(CH₃)— | —C₈H₁₇ | |
| 11 | Cl | Cl | —CH(CH₃)— | —C₁₂H₂₅ | |
| 12 | Cl | Cl | —CH(CH₃)— | —CH—CH=CH₂ | |
| 13 | Cl | Cl | —CH(CH₃)— | —CH₂—COOC₂H₅ | |
| 14 | Cl | Cl | —CH(CH₃)— | —C₆H₅ | |
| 15 | Cl | Cl | —CH(CH₃)— | —CH₂—C₆H₅ | |
| 16 | Cl | Cl | —CH(CH₃)— | —CH₂—C₆H₄—Cl | |
| 17 | Cl | Cl | —CH(CH₃)— | —CH₂—C₆H₄—OCH₃ | |
| 18 | Cl | Cl | —CH(CH₃)— | —C₃H₆—C₆H₅ | |
| 19 | Cl | Cl | —CH(CH₃)— | —C₆H₅ | |
| 20 | Cl | Cl | —CH(CH₃)— | —C₆H₄—F | |
| 21 | Cl | Cl | —CH(CH₃)— | —C₆H₄—NO₂ | |
| 22 | Cl | Cl | —CH(CH₃)— | —C₆H₄—OCH₃ | |
| 23 | Cl | Cl | —CH(CH₃)— | —C₆H₃(CH₃)(Br) | $n_D^{30}$ 1.6100 |
| 24 | Cl | Cl | —CH(CH₃)— | —CH₂-(furyl) | |
| 25 | Cl | Cl | —CH(CH₃)— | —(pyridyl) | |
| 26 | Cl | Cl | —CH(CH₃)— | —(thiazolyl) | m.p. 152° |

The inhibition of growth effected by the 3-pyridinol compounds according to the invention was determined by the following tests:

Inhibition of Growth in Soya Bean Crops

The 3-pyridinol compounds of formula I inhibit the excessive vegetative growth of soya bean plants and thus render possible an increase of yield. Comparisons of yield were made in a field test in the case of various species of soya bean.

Plots of about 50 m² were sprayed in the blossom period with an aqueous preparation of compounds of formula I to the extent that the spraying corresponded to applying an amount of 1 kg of active substance per hectare. This treatment was repeated 5 times in each test. At the same time, a corresponding number of plots were left as untreated control plots. At the time of harvesting, the mean growth in height of the plants and the yield were determined for each plot.

Compared with the soya bean plants grown on the control plots, those grown on the plots treated with the compounds No. 1, 6 or 12 displayed a 5–10% reduction in growth in height and approx. a 5% increase in yield.

Inhibition of the Growth of Undesirable Side Shoots on Tobacco Plants

Tobacco plants of the variety "Xanti" were grown in a greenhouse and shortly before blossoming were topped (the leading shoot was cut off). One day after topping, 3 plants in each case were each sprayed from the top with 10 ml of aqueous preparations of a compound of formula I. The selected concentrations of active substance corresponded in a normal plant population to applied amounts of 12 kg, 6 kg and 3 kg of active substance per hectare, respectively. Fourteen days after application, the inhibitory action on the undesirable growth of side shoots was evaluated. For this purpose, the average length of the side shoots from the 6 uppermost leaf axils of all three plants was determined.

The plants treated with the compounds 6, 12 and 14 showed no growth, or just a very slight growth, of the side shoots, which in the case of the untreated control plants had attained an average length of over 20 cm.

The compositions according to the invention are produced in a manner known per se by the intimate mixing and/or grinding of active substances of the general formula I with suitable carriers, optionally with the addition of dispersing agents or solvents which are inert to the active substances. The active substances can be used as dusts, scattering agents, granulates (coated granulates, impregnated granulates and homogeneous granulates), wettable powders, pastes, emulsions, solutions or aerosols.

The solid preparations (dusts, scattering agents and granulates) are produced by the mixing of the active substances with solid carriers. The particle size of the carriers is for dusts advantageously up to about 0.1 mm; for scattering agents about 0.075 to 0.2 mm; and for granulates 0.2 mm or coarser.

The concentration of active substance in the solid preparations is as a rule 0.5 to 80%. It is possible to add to these mixtures also additives stabilising the active substance, and/or nonionic, anion-active and cation-active substances which improve, e.g., the adhesiveness of the active substances on plants and parts of plants (adhesives and agglutinants), and/or ensure better wettability (wetting agents) as well as dispersibility (dispersing agents).

Water-dispersible concentrates of active substances, i.e. wettable powders, pastes and emulsion concentrates, are agents which can be diluted with water to obtain any desired concentration. They consist of active substance, carrier, optionally additives stabilising the active substance, surface-active substances and antifoaming agents and, optionally, solvents. The concentration of active substance in these preparations is 5–80%. The wettable powders and pastes are obtained by the mixing and grinding of the active substances with dispersing agents and pulverulent carriers, in suitable devices, until homogeneity is obtained. In some cases it is advantageous to use mixtures of various carriers. Suitable anti-foaming agents are, e.g., silicones. The active substances are so mixed, ground, sieved and strained with the aforementioned additives that the solid constituent in the case of wettable powders has a particle size not exceeding 0.02 to 0.04 mm, and in the case of pastes not exceeding 0.003 mm. Dispersing agents, organic solvents and water are used to produce emulsion concentrates and pastes. The solvents must be practically odourless, nonphytotoxic, inert to the active substances and not readily combustible.

Furthermore, the agents according to the invention can be used in the form of solutions. For this purpose, the active substance, or several active substances, of the general formula I is (or are) dissolved in suitable organic solvents, solvent mixtures or water. The solutions should contain the active substances in a concentration of 1 to 20%.

Other biocidal active substances or agents can be mixed with the described compositions of the invention. For the broadening or their sphere of action, the new compositions can for example contain, in addition to the stated compounds of the general formula I and other herbicides: insecticides, fungicides, bactericides, fungistatics, bacteriostatics or nematocides. The compositions of the invention may also contain fertilisers, trace elements, etc.

Granulate

The following substances are used to produce a 5% granulate:
5 parts of 2-[(2,6-dichloro-3-pyridyl)-oxy]-propionic acid ethyl ester,
0.25 part of epichlorohydrin,
0.25 part of cetyl polyglycol ether with 8 moles of ethylene oxide,
0.50 parts of polyglycol ("Carbowax"),
91 parts of kaolin (particle size 0.3–0.8 mm).

The active substance is mixed with epichlorohydrin and the mixture is dissolved in 6 parts of acetone; the polyglycol and cetyl polyglycol ether are then added. The resulting solution is sprayed onto kaolin and the acetone is subsequently evaporated off in vacuo.

Wettable Powders

The following constituents are used to produce (a) a 50%, (b) a 25% and (c) a 10% wettable powder:
(a)
  50 parts of 2-[(2,6-dichloro-3-pyridyl)-oxy]-propionic acid methyl ester,
  5 parts of sodium dibutyl-naphthalene sulphonate,
  3 parts of naphthalenesulphonic acid/phenolsulphonic acid/formaldehyde condensate 3:2:1,
  20 parts of kaolin,
  22 parts of Champagne chalk;
(b) 25 parts of the above Active Substance,
  5 parts of the sodium salt of oleyl methyl tauride,
  2.5 parts of naphthalenesulphonic acid/formaldehyde condensate,
  0.5 part of carboxymethylcellulose,
  5 parts of neutral potassium aluminum silicate,
  62 parts of kaolin;
(c) 10 parts of the above Active Substance,
  3 parts of a mixture of the sodium salts of saturated fatty alcohol sulphates,
  5 parts of naphthalenesulphonic acid/formaldehyde condensate,
  82 parts of kaolin.

The given active substance is absorbed onto the appropriate carriers (kaolin and chalk) and subsequently mixed and ground with the other constituents. Wettable powders having excellent wetting and suspension properties are obtained. It is possible to obtain from such wettable powders, by dilution with water, suspensions of the desired concentration. These suspensions can be used to control weeds and wild grasses in cotton crops.

Paste

The following substances are used to produce a 45% paste:
45 parts of (2,6-dichloro-3-pyridyl)oxy-acetic acid,
5 parts of sodium aluminium silicate,
14 parts of cetyl polyglycol ether with 8 moles of ethylene oxide,
1 part of cetyl polyglycol ether with 5 moles of ethylene oxide,
2 parts of spindle oil,
10 parts of polyglycol (Carbowax),
23 parts of water.

The active substance is intimately mixed and ground with the additives in suitable devices. A paste is obtained from which it is possible to produce, by dilution with water, suspensions of the desired concentration.

Emulsion concentrate

The following constituents are mixed together to produce a 10% emulsion concentrate:
10 parts of 2-[(2,6-dichloro-3-pyridyl)-oxy]-propionic acid ethyl ester,
15 parts of oleyl polyglycol ether with 8 moles of ethylene oxide, 75 parts of isophorone (3,5,5-trimethylcyclohex-2-en-1-one).

This concentrate can be diluted with water to give emulsions of a suitable concentration. Such emulsions are suitable for combatting weeds in cultivated crops, such as in crops of soya beans and potatoes.

We claim:

1. 2-[(2,6-dichloro-3-pyridyl)-oxy-]-propionic acid 6'-chlorohexyl ester.

2. 2-[(2,6-dichloro-3-pyridyl)-oxy]-propionic acid allyl ester.

3. 2-[(2,6-dichloro-3-pyridyl)-oxy]-propionic acid benzyl ester.

4. A composition for inhibiting dicotyledonous plant growth, which comprises (1) as active substance a plant growth inhibiting effective amount of a compound according to claim 1 and (2) an inert carrier.

5. A composition for inhibiting dicotyledonous plant growth, which comprises (1) as active substance a plant growth inhibiting effective amount of a compound according to claim 2 and (2) an inert carrier.

6. A composition for inhibiting dicotyledonous plant growth, which comprises (1) as active substance a plant growth inhibiting effective amount of a compound according to claim 3 and (2) an inert carrier.

7. A method for inhibiting the growth of dicotyledonous plants which comprises applying to said plants a growth inhibiting effective amount of a compound according to claim 1.

8. A method for inhibiting the growth of dicotyledonous plants which comprises applying to said plants a growth inhibiting effective amount of a compound according to claim 2.

9. A method for inhibiting the growth of dicotyledonous plants which comprises applying to said plants a growth inhibiting effective amount of a compound according to claim 3.

10. A method according to claim 7 in which the plants are soya bean plants.

11. A method according to claim 8 in which the plants are soya bean plants.

12. A method according to claim 9 in which the plants are soya bean plants.

* * * * *